US006602699B2

(12) United States Patent
Kozian et al.

(10) Patent No.: US 6,602,699 B2
(45) Date of Patent: Aug. 5, 2003

(54) PROMOTOR FOR FUNCTIONAL CHARACTERIZATION OF G-PROTEIN COUPLED RECEPTORS IN THE YEAST SACCHAROMYCES CEREVISIAE

(75) Inventors: Detlef Kozian, Hattersheim (DE); Almut Nitsche, Wiesbaden (DE); Pauline Fraissignes, Munich (DE); Sabine Gratzer, Graefelfing (DE); Ekkehard Leberer, Germering (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 09/986,121

(22) Filed: Nov. 7, 2001

(65) Prior Publication Data

US 2003/0059779 A1 Mar. 27, 2003

(30) Foreign Application Priority Data

Nov. 16, 2000 (DE) ........................................ 100 56 899

(51) Int. Cl.[7] ........................... C12N 15/11; C12N 1/15; C12N 15/63

(52) U.S. Cl. .............................. 435/254.21; 435/320.1; 536/24.1

(58) Field of Search ...................... 536/24.1; 435/320.1, 435/243, 419, 325, 254.21

(56) References Cited

U.S. PATENT DOCUMENTS 5,063,154 A 11/1991 Fink et al.

FOREIGN PATENT DOCUMENTS

| | | |
|---|---|---|
| WO | WO 99/51620 | 10/1999 |
| WO | WO 00/12704 | 3/2000 |
| WO | WO 01/16378 A2 | 3/2001 |

OTHER PUBLICATIONS

Pausch M H., G–Protein–Coupled Receiptors in *Sacchromyces cerevisiae*: High–Throughput Screening Assays for Drug Discovery; *Trends In Biotechnology, Elsevier Publications, Cambridge, GB*, Dec. 1, 1997; vol. 15, pp. 487–494.

XP–002217914—May 6, 1996, Retrieved from EBI Database Accession No. Z71555.

Mary J. Cismowski et al., "Genetic screens in yeast to identify mammalian nonreceptor modulators of G–protein signaling", Nature Biotechnology, Sep. 1999, pp. 878–883, vol. 17.

Scott Erdman et al., "Pheromone–regulated Genes Required for Yeast Mating Differentiation", J. Cell Biol., pp. 461–83, vol. 140.

Robert M. Frederickson, "Budding actors in mammalian G–protein signaling", Nature Biotechnology, Sep. 1999, pp. 852–853, vol. 17.

Elizabeth Geras–Raaka et al., "Human Interferon–y–inducible Protein 10 (IP–10) Inhibits Constitutive Signaling of Kaposi's Sarcoma–associated Herpesvirus G Protein–coupled Receptor", J. Exp. Med., Jul. 20, 1998, pp. 405–408, vol. 188, No. 2.

Michael C. Gustin et al., "MAP Kinase Pathways in the Yeast *Saccharomyces cerevisiae*", Microbiology and Molecular Biology Reviews, Dec. 1998, pp. 1264–1300, vol. 62, No. 4.

Hisao Ito, et al., "Transformation of Intact Yeast Cells Treated with Alkali Cations", Journal of Bacteriology, Jan. 1983, pp. 163–168, vol. 153, No. 1.

Petra Ross–MacDonald et al., "Large–scale analysis of the yeast genome by transposon tagging and gene disruption", Nature, Nov. 25, 1999, pp. 413–419, vol. 402.

Jeffrey M. Stadel et al., "Orphan G protein–coupled receptors: a neglected opportunity for pioneer drug discovery", Tips, Nov. 1997, pp. 430–437, vol. 18.

Shelagh Wilson et al., "Orphan G–protein–coupled receptors: the next generation of drug targets?", British Journal of Pharmacology, 1998, pp. 1387–1392, vol. 125.

Lisa Wodicka et al., "Genome–wide expression monitoring in *saccharomyces cerevisiae*", Nature Biotechnology, Dec. 1997, vol. 15.

*Primary Examiner*—Terry McKelvey
(74) *Attorney, Agent, or Firm*—Heller Ehrman White and McAuliffe

(57) ABSTRACT

The present invention relates to a promoter, to DNA fragments containing said promoter and to the use thereof, in particular in methods for identifying substances exhibiting an activating or inhibiting action on G protein-coupled receptors.

12 Claims, 11 Drawing Sheets

FIG. 1a-1

```
-505  CCTTT
-500  TATTCTCTAC ACCGAATTTG TCTTTACTCC TATGCTGTTT ACAAGGTCTA
-450  TCTGATAAGC AATTGCGCAA GAAAATAGTA GAATGAAAAC TGATTATTAA
-400  AAACAAACGT AAACTCAAGC CTCACTTGAT GCTCAGACGG AGTACGTGAA
-350  AAACGTCCGT TATGCAAAAC CCTTTATATG CACAACCTTC ACACAATGCA
-300  AATTTCCGAT GATGCCTACA TACAAAAGAG CGAAAGGCGA TATAAATTTT
-250  TTTCACGGGA TTTTCGTTTA GGTGAAAATA AAATGAACGA CAGAGCATGC
-200  AGAGTCCGGG TAATACATAT GTTTCAATAC TGTTTCAATA CTGTTTCAGA
-150  AGTGCGTCAC ATATTAATTT TAACTTATAA CTGGCCTGTT GCTGGCAAGA
-100  GGTATATATA TATGACGAAT GTGACCAACA TAAGTCCTTA AGATAATCCC
-50   GAAATATTTG GTTAGGATGA TTCCCTTTCG AATTTGTGAA CGTTGATGAT
+1    ATGAGCGGTT TTAAATGCTA TTTGCAATTG GGTGACAGGC TCTCTCAAAT
+50   ATGGCTAAAT AAGTATACTT TGGTTTTGCT GCTAGCAATG CTGAAGCTTC
+100  TGTTTTTCTC CAAATCCATA CAACATGCGA TAGAAGTCTC GGAAACGTAT
+150  ATTTTGTCCA ATTGTTACAG TATTGATTCA CTATACTCCA AGATGACAGA
+200  CAACACGCCG CACTATTTAG GTATCATGGG GAATTATCTT ATCGAGAAGG
+250  GTATGGAGGA GACTGTTAAA GCTACGCTAG AGACGTTATC ACTTATAGTA
+300  TATGCGAGCG AGGGGCTGGT AAACTTTGCC ATTGACCTGT ATTTGGGCAC
+350  TTATGCCTGT TTGATTGTTA GTGCCGTTGA TGGTACCGTG GACGTTGCTA
+400  CTAACATTAC AGAAAAACTG ATTAGCTTAG TCAATGATAC AGTTTCAAGT
+450  GTGGCTAATG AATTGGATAC GGGCTTGAAT GACATCTCCA AAATAATCAA
+500  TAAAGTGATC AAGGCCGCAT CCAAAGTAGA GAATTTTTTC ACAGGTGATG
+550  ACGATGACAG TAACATGACG TCGTCAATCA AAAGCGTCAA CTTAACCATA
+600  TCTGCGCTTC ACAATTTATA CATTCCTTCC TCAATCAACG ATAAGCTTGA
+650  AGAGTTATCG GCAAAGACGC CGGACTTTGC CCAGGTTAAG AATACAACCA
+700  AGAACCTGAT CTCGGTTCCC TTCAATGAAG TTCGGAAGAA TATCAAGGCC
+750  GTGAATGCCA GCAATATAAT CGGAGATACC TCCGTTTTGT ACGTACCTCC
+800  CGTGTCCCTT GACAACAGTA CTGGGATTTG CTCATCCAAT CAATCAGAAA
+850  TTTTGGCCTT TTATTCCATC TTGGGACATG TCCTGAAAAT AGCCACCGTA
+900  GTGTGCATTA CCGTATTGAT ATGCTTCGCT GTTGGTGCGA TGGCGCCCGT
+950  TGCATGGAAT GAAATCAAGC TCTGGAGGCG CCTTTGCGGA ATGAGAGACC
+1000 ATTACATGCT GAGCAGGCAA GATTCGTATA CGTCCTTTTC CAGTGAAAAC
+1050 ACGCACGAAT TGAAAGATCC ATTTAGAGAT CCTCCTATAC AAAATGGCCA
+1100 ATATGATGTC ATTGCAAGCT ATCAGCAGTG CTTTCAAACA TGGAACACAA
```

FIG. 1a-2

```
+1150 GAATAGCAGG CTGGATGACA AATCTTGTTA CCTTTGGAAA ATCACCAGAG
+1200 AACATTGACC CAAAGACTAA ACAAAAAATA GAATGGGTAG TGGCTTATAT
+1250 GACCTCCGAA AGAGCACTGT GTGTTCTTGG AATTGGACTT TTGGGAATTT
+1300 TAGTGTGCAT ATGCCAATTT GTCATGATAG CACTGTTAAA ACACAAGATA
+1350 AGCCATTCAT TGACTTCTAA TGATGGTGAC GGCGTTCAAA ATTTGCTGAA
+1400 GTCTAGCACT GCCGTCGATA TAGAGAACCA AATGAGCCTT TGGAGCGTTC
+1450 AGACTAATAA ATATATAAAT ACTACGGAGA CCAATATCAA TCAGGAAGTA
+1500 TTCGGGTGGA TAAACACGAC AACACTTTCT GTGAACAATA CAGTGGCCAC
+1550 CATGATCTCT GATATAGACA CAACTTTAGC AGATGTATTC AATGGAACAC
+1600 TGCTATATAA CCCAATGAAA ACCGTGGTCG GATGTGCCAT TGAAAATAAG
+1650 CTCTACACAA TAGAGAAGGC AATGACGTGG ATTCACGACA AGGCTCAGCT
+1700 GCATATCCCG AGAATTAATG GGACACAAAT CAAGCAAGCT CTGGCAAAGC
+1750 AAACCGACAA CAGCACTATA CCCACTGCAA GCTCCACTTC TGCCGCCACA
+1800 GAAAACTTAC TGGAGAACCT TGTGAATGAT ATGAGAGAAG GACTTTTAAA
+1850 AATTCTCCGA GCTTACCACC GTATAACTCT GGGAGAACTC ACGGTAGCCT
+1900 TGGTCATTCT TGCGGTGTGG CTCGTACAAT TGCCCATAGC TCTGGTAATT
+1950 CTCCGATTAC GTCTTCGCAA AGCCACCTTT GACTGATTAA TTAGTTGATA
+2000 GACTTTTTCC GTCATAACTC TATTTAATAA TGATGACCAA AAAGAGGCTC
+2050 GTTCGAATCA TTTCGCGTTG AATTTGAAAT TCGCGGAGGA AAAACACGCA
+2100 AAGAGAATCG GAAACCTTAT CGTCAAATCA TTGCACCTTG CAATGGTGGG
+2150 TAATGATACA TCATCGCAGT AACAGTATTC ATATATTCGT ATAGTTAATA
+2200 AGATCACTTT TCAGTTAGCT TATACAATAA AAGATATTAC CTTTTGTATT
+2250 GTTAGTTGCA ACATCCTTTT TTTATAAACT TTGACAGGCG ATATTACGTT
+2300 TGTCACTTCG GTTTCCCCAC ACAAAGAACA CGTTACTTGG CAAATTCAGC
+2350 TCTT
```

|

CCTTT

FIG. 1b-2

```
-500                                                      -451
|                                                            |
TATTCTCTAC ACCGAATTTG TCTTTACTCC TATGCTGTTT ACAAGGTCTA

-450                                                      -401
|                                                            |
TCTGATAAGC AATTGCGCAA GAAAATAGTA GAATGAAAAC TGATTATTAA

-400                                                      -351
|                                                            |
AAACAAACGT AAACTCAAGC CTCACTTGAT GCTCAGACGG AGTACGTGAA

-350                                                      -301
|                                                            |
AAACGTCCGT TATGCAAAAC CCTTTATATG CACAACCTTC ACACAATGCA

-300                                                      -251
|                                                            |
AATTTCCGAT GATGCCTACA TACAAAAGAG CGAAAGGCGA TATAAATTTT

-250                                                      -201
|                                                            |
TTTCACGGGA TTTTCGTTTA GGTGAAAATA AAATGAACGA CAGAGCATGC

-200                                                      -151
|                                                            |
AGAGTCCGGG TAATACATAT GTTTCAATAC TGTTTCAATA CTGTTTCAGA

-150                                                      -101
|                                                            |
AGTGCGTCAC ATATTAATTT TAACTTATAA CTGGCCTGTT GCTGGCAAGA

-100                                                       -51
|                                                            |
GGTATATATA TATGACGAAT GTGACCAACA TAAGTCCTTA AGATAATCCC
```

FIG. 1b-3

```
-50                                                    -1
|                                                       |
GAAATATTTG GTTAGGATGA TTCCCTTTCG AATTTGTGAA CGTTGATGAT

+1                                                    +50
|                                                       |
ATGAGCGGTT TTAAATGCTA TTTGCAATTG GGTGACAGGC TCTCTCAAAT
```

FIG. 1c

TGTTTCA Consensus sequence

| | Mismatch | |
|---|---|---|
| -354 -348<br>5'-TGAAAAA-3' | 1 | Inverse orientation to consensus sequence |
| -252 -246<br>5'-TTTTTCA-3' | 1 | Consensus sequence |
| -181 -175<br>5'-TGTTTCA-3' | 0 | Consensus sequence |
| -170 -164<br>5'-TGTTTCA-3' | 0 | Consensus sequence |
| -159 -153<br>5'-TGTTTCA-3' | 0 | Consensus sequence |

sst1Δ far1/sst1Δ

FIG. 4(A)

| | pYNL279(L)-AEQ | | | Control vector | | | 4PRE-AEQ | | |
|---|---|---|---|---|---|---|---|---|---|
| | 1 | 2 | 3 | 1 | 2 | 3 | 1 | 2 | 3 |
| α factor log [M] | | | | | | | | | |
| -12 | 32.0 | 22.7 | 55.9 | 0.3 | 0.1 | 0.1 | 45.1 | 35.3 | 55.2 |
| -11 | 42.4 | 31.2 | 64.3 | 0.1 | 0.1 | 0.1 | 48.5 | 34.4 | 52.7 |
| -10 | 36.9 | 24.9 | 65.8 | 0.1 | 0.1 | 0.1 | 47.1 | 31.6 | 67.1 |
| -9 | 128.4 | 88.2 | 179.0 | 0.1 | 0.1 | 0.1 | 87.2 | 55.0 | 88.5 |
| -8 | 563.5 | 335.9 | 793.0 | 0.1 | 0.1 | 0.1 | 230.0 | 161.9 | 460.1 |
| -7 | 1,328.0 | 551.2 | 1,715.0 | 0.1 | 0.1 | 0.1 | 441.2 | 295.4 | 893.1 |
| -6 | 1,152.0 | 455.9 | 1,551.0 | 0.1 | 0.1 | 0.0 | 433.1 | 268.6 | 865.7 |

pYNL279-AEQ
4PRE-AEQ
Control vector
Alpha factor [M]
log scale
Relative light units
1400.0
1200.0
1000.0
800.0
600.0
400.0
200.0
0.0
-12 -11 -10 -9 -8 -7 -6
pYNL279-AEQ 36.9 46.0 42.5 131.9 564.1 1198.1 1053.0
4PRE-AEQ 45.2 45.2 48.6 76.9 284.0 543.2 522.5
Control vector 0.1 0.1 0.1 0.1 0.1 0.1 0.1

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Primer YNL279F1

<400> SEQUENCE: 1

ccgagtccta ctcctatgct gtttacaagg                                   30


<210> SEQ ID NO 2
<211> LENGTH: 31
<212> TYPE: DNA
<213> ORGANISM: Artificial Sequence
<220> FEATURE:
<223> OTHER INFORMATION: Primer YNL279R

<400> SEQUENCE: 2

tgctctagaa tcatcaacgt tcacaaattc g                                 31


<210> SEQ ID NO 3
<211> LENGTH: 2859
<212> TYPE: DNA
<213> ORGANISM: Saccharomyces cerevisiae

<400> SEQUENCE: 3

ccttttattc tctacaccga atttgtcttt actcctatgc tgtttacaag gtctatctga    60

taagcaattg cgcaagaaaa tagtagaatg aaaactgatt attaaaaaca aacgtaaact   120

caagcctcac ttgatgctca gacggagtac gtgaaaaacg tccgttatgc aaaacccttt   180

atatgcacaa ccttcacaca atgcaaattt ccgatgatgc ctacatacaa aagagcgaaa   240

ggcgatataa atttttttca cgggattttc gtttaggtga aaataaaatg aacgacagag   300

catgcagagt ccgggtaata catatgtttc aatactgttt caatactgtt tcagaagtgc   360

gtcacatatt aattttaact tataactggc ctgttgctgg caagaggtat atatatatga   420

cgaatgtgac caacataagt ccttaagata atcccgaaat atttggttag gatgattccc   480

tttcgaattt gtgaacgttg atgatatgag cggttttaaa tgctatttgc aattgggtga   540

caggctctct caaatatggc taaataagta tactttggtt ttgctgctag caatgctgaa   600
```

-continued

```
gcttctgttt ttctccaaat ccatacaaca tgcgatagaa gtctcggaaa cgtatatttt    660
gtccaattgt tacagtattg attcactata ctccaagatg acagacaaca cgccgcacta    720
tttaggtatc atggggaatt atcttatcga gaagggtatg gaggagactg ttaaagctac    780
gctagagacg ttatcactta tagtatatgc gagcgagggg ctggtaaact ttgccattga    840
cctgtatttg ggcacttatg cctgtttgat tgttagtgcc gttgatggta ccgtggacgt    900
tgctactaac attacagaaa aactgattag cttagtcaat gatacagttt caagtgtggc    960
taatgaattg gatacgggct tgaatgacat ctccaaaata atcaataaag tgatcaaggc   1020
cgcatccaaa gtagagaatt ttttcacagg tgatgacgat gacagtaaca tgacgtcgtc   1080
aatcaaaagc gtcaacttaa ccatatctgc gcttcacaat ttatacattc cttcctcaat   1140
caacgataag cttgaagagt tatcggcaaa gacgccggac tttgcccagg ttaagaatac   1200
aaccaagaac ctgatctcgg ttcccttcaa tgaagttcgg aagaatatca aggccgtgaa   1260
tgccagcaat ataatcggag atacctccgt tttgtacgta cctcccgtgt cccttgacaa   1320
cagtactggg atttgctcat ccaatcaatc agaaattttg gccttttatt ccatcttggg   1380
acatgtcctg aaaatagcca ccgtagtgtg cattaccgta ttgatatgct tcgctgttgg   1440
tgcgatggcg cccgttgcat ggaatgaaat caagctctgg aggcgccttt gcggaatgag   1500
agaccattac atgctgagca ggcaagattc gtatacgtcc ttttccagtg aaaacacgca   1560
cgaattgaaa gatccattta gagatcctcc tatacaaaat ggccaatatg atgtcattgc   1620
aagctatcag cagtgctttc aaacatggaa cacaagaata gcaggctgga tgacaaatct   1680
tgttaccttt ggaaaatcac cagagaacat tgacccaaag actaaacaaa aaatagaatg   1740
ggtagtggct tatatgacct ccgaaagagc actgtgtgtt cttggaattg gacttttggg   1800
aattttagtg tgcatatgcc aatttgtcat gatagcactg ttaaaacaca agataagcca   1860
ttcattgact tctaatgatg gtgacggcgt tcaaaatttg ctgaagtcta gcactgccgt   1920
cgatatagag aaccaaatga gcctttggag cgttcagact aataaatata taaatactac   1980
ggagaccaat atcaatcagg aagtattcgg gtggataaac acgacaacac tttctgtgaa   2040
caatacagtg gccaccatga tctctgatat agacacaact ttagcagatg tattcaatgg   2100
aacactgcta tataacccaa tgaaaaccgt ggtcggatgt gccattgaaa ataagctcta   2160
cacaatagag aaggcaatga cgtggattca cgacaaggct cagctgcata tcccgagaat   2220
taatgggaca caaatcaagc aagctctggc aaagcaaacc gacaacagca ctatacccac   2280
tgcaagctcc acttctgccg ccacagaaaa cttactggag aaccttgtga atgatatgag   2340
agaaggactt ttaaaaattc tccgagctta ccaccgtata actctgggag aactcacggt   2400
agccttggtc attcttgcgg tgtggctcgt acaattgccc atagctctgg taattctccg   2460
attacgtctt cgcaaagcca cctttgactg attaattagt tgatagactt tttccgtcat   2520
aactctattt aataatgatg accaaaaaga ggctcgttcg aatcatttcg cgttgaattt   2580
gaaattcgcg gaggaaaaac acgcaaagag aatcggaaac cttatcgtca aatcattgca   2640
ccttgcaatg gtgggtaatg atacatcatc gcagtaacag tattcatata ttcgtatagt   2700
taataagatc acttttcagt tagcttatac aataaaagat attacctttt gtattgttag   2760
ttgcaacatc cttttttat aaactttgac aggcgatatt acgtttgtca cttcggtttc   2820
cccacacaaa gaacacgtta cttggcaaat tcagctctt                          2859

<210> SEQ ID NO 4
```

-continued

<211> LENGTH: 670
<212> TYPE: DNA
<213> ORGANISM: Saccharomyces cerevisiae
<220> FEATURE:
<221> NAME/KEY: misc_feature
<222> LOCATION: (560)..(560)
<223> OTHER INFORMATION: n is A, C, T or G
<220> FEATURE:
<221> NAME/KEY: misc_feature
<222> LOCATION: (571)..(571)
<223> OTHER INFORMATION: n is A, C, T or G
<220> FEATURE:
<221> NAME/KEY: misc_feature
<222> LOCATION: (573)..(573)
<223> OTHER INFORMATION: n is A, C, T or G
<220> FEATURE:
<221> NAME/KEY: misc_feature
<222> LOCATION: (577)..(577)
<223> OTHER INFORMATION: n is A, C, T or G
<220> FEATURE:
<221> NAME/KEY: misc_feature
<222> LOCATION: (592)..(592)
<223> OTHER INFORMATION: n is A, C, T or G
<220> FEATURE:
<221> NAME/KEY: misc_feature
<222> LOCATION: (597)..(597)
<223> OTHER INFORMATION: n is A, C, T or G
<220> FEATURE:
<221> NAME/KEY: misc_feature
<222> LOCATION: (600)..(600)
<223> OTHER INFORMATION: n is A, C, T or G
<220> FEATURE:
<221> NAME/KEY: misc_feature
<222> LOCATION: (604)..(604)
<223> OTHER INFORMATION: n is A, C, T or G
<220> FEATURE:
<221> NAME/KEY: misc_feature
<222> LOCATION: (606)..(606)
<223> OTHER INFORMATION: n is A, C, T or G
<220> FEATURE:
<221> NAME/KEY: misc_feature
<222> LOCATION: (610)..(610)
<223> OTHER INFORMATION: n is A, C, T or G
<220> FEATURE:
<221> NAME/KEY: misc_feature
<222> LOCATION: (619)..(619)
<223> OTHER INFORMATION: n is A, C, T or G
<220> FEATURE:
<221> NAME/KEY: misc_feature
<222> LOCATION: (621)..(621)
<223> OTHER INFORMATION: n is A, C, T or G
<220> FEATURE:
<221> NAME/KEY: misc_feature
<222> LOCATION: (625)..(625)
<223> OTHER INFORMATION: n is A, C, T or G
<220> FEATURE:
<221> NAME/KEY: misc_feature
<222> LOCATION: (634)..(634)
<223> OTHER INFORMATION: n is A, C, T or G
<220> FEATURE:
<221> NAME/KEY: misc_feature
<222> LOCATION: (636)..(636)
<223> OTHER INFORMATION: n is A, C, T or G
<220> FEATURE:
<221> NAME/KEY: misc_feature
<222> LOCATION: (640)..(640)
<223> OTHER INFORMATION: n is A, C, T or G
<220> FEATURE:
<221> NAME/KEY: misc_feature
<222> LOCATION: (649)..(649)
<223> OTHER INFORMATION: n is A, C, T or G
<220> FEATURE:
<221> NAME/KEY: misc_feature
<222> LOCATION: (651)..(651)
<223> OTHER INFORMATION: n is A, C, T or G
<220> FEATURE:
<221> NAME/KEY: misc_feature
<222> LOCATION: (655)..(655)
<223> OTHER INFORMATION: n is A, C, T or G -continued

```
<220> FEATURE:
<221> NAME/KEY: misc_feature
<222> LOCATION: (664)..(664)
<223> OTHER INFORMATION: n is A, C, T or G
<220> FEATURE:
<221> NAME/KEY: misc_feature
<222> LOCATION: (666)..(666)
<223> OTHER INFORMATION: n is A, C, T or G
<220> FEATURE:
<221> NAME/KEY: misc_feature
<222> LOCATION: (670)..(670)
<223> OTHER INFORMATION: n is A, C, T or G

<400> SEQUENCE: 4

cctttattc tctacaccga atttgtcttt actcctatgc tgtttacaag gtctatctga     60

taagcaattg cgcaagaaaa tagtagaatg aaaactgatt attaaaaaca aacgtaaact   120

caagcctcac ttgatgctca gacggagtac gtgaaaaacg tccgttatgc aaaacccttt   180

atatgcacaa ccttcacaca atgcaaattt ccgatgatgc ctacatacaa aagagcgaaa   240

ggcgatataa atttttttca cgggattttc gtttaggtga aaataaaatg aacgacagag   300

catgcagagt ccgggtaata catatgtttc aatactgttt caatactgtt tcagaagtgc   360

gtcacatatt aattttaact tataactggc ctgttgctgg caagaggtat atatatatga   420

cgaatgtgac caacataagt ccttaagata atcccgaaat atttggttag gatgattccc   480

tttcgaattt gtgaacgttg atgatatgag cggttttaaa tgctatttgc aattgggtga   540

caggctctct caaatabbdn gctgtttcac nsnsssnmsm atchtgaaaa anvrsrntrn   600

grcnsnsssn tttttcacns nsssntgttt cacnsnsssn tgtttcacns nsssntgttt   660

cacnsnsssn                                                          670
```

PROMOTOR FOR FUNCTIONAL CHARACTERIZATION OF G-PROTEIN COUPLED RECEPTORS IN THE YEAST SACCHAROMYCES CEREVISIAE

The present invention relates to a promoter, to DNA fragments containing said promoter and to the use thereof, in particular in methods for identifying substances exhibiting an activating or inhibiting action on G protein-coupled receptors.

GPCRs (G protein-coupled receptors) form a gene family of structurally and functionally linked transmembrane proteins. GPCRs are target molecules of great importance for medical research and the development of pharmacological active substances and occupy a key position in a multiplicity of pathologies (Stadel et al., 1997). The classic example of the central position of GPCRs in the pharmacological treatment of asthma is $\beta_2$AR ($\beta_2$-adrenergic receptor) or the involvement of a Kaposi sarcoma (KS)-associated herpesvirus GPCR in KS pathogenesis (Geras-Raaka et al., 1998). This class of receptors bind a broad spectrum of ligands such as, for example, protein hormones, chemokines, peptides or divalent cations. The identification of activators and inhibitors of G protein-coupled receptors is thus one of the most promising approaches toward a better knowledge and treatment of diseases (Wilson et al., 1998).

Many components of the GPCR signal transduction pathway have orthologous components in the GPCR signal transduction pathway of bakers' yeast, *Saccharomyces cerevisiae*. Stimulation with mating factor (pheromone α or pheromone a) activates, for example, the pheromone-dependent mitogen-activated protein kinase cascade (denoted MAPK cascade hereinbelow) (Frederickson, 1999). This property of yeast can be utilized for assaying mammalian GPCRs, in particular human GPCRs, in a yeast model, in order to search for activators or inhibitors of the relevant GPCR or the corresponding signal transduction pathway, in particular since GPCRs of foreign species can be functionally expressed in yeast, resulting via the yeast MAPK cascade in a measurable cellular response when the introduced GPCR is activated by a specific ligand and this signal is passed on to the yeast MAPK cascade. The search for activators or inhibitors of GPCRs to which, up until now, no functions have been ascribed, the "orphan GPCRs", is of particular interest.

The pheromones α and a act in *S. cerevisiae* via the endogenous G protein-coupled receptors Ste2p und Ste3p (Gustin et al., 1998). In this connection, pheromone α acts directly on the pheromone-dependent MAPK cascade, thereby regulating the expression of particular *S. cerevisiae* genes. Whether a substance acts in an activating or inhibiting way on a GPCR heterologously expressed in *S. cerevisiae*, may be detected by expressing the *S. cerevisiae* genes which are regulated by the MAPK cascade (marker genes). The promoters of such marker genes may be used, for example in connection with a suitable reporter system, for identifying GPCR activators or inhibitors.

Pheromone-regulated genes may be identified either by using transposon mutagenesis (Ross-Macdonald et al., 1999) or by using DNA microchips, which allows expression analysis of all mRNAs of a cell at a particular time (Wodicka et al., 1997).

Up until now, functional assays for identifying inhibitors or activators of GPCRs have been carried out mainly in mammalian cells (Wilson et al. (1998) British Journal of Pharmacology 125, 1387–1392; Geras-Raaka et al. (1998) J. Exp. Med. 188 No.2, 405–408). The use of promoters of the FUS1 and FUS2 genes for functional assays in *S. cerevisiae* has been described (Cisnowski et al. (1999) Nature 17, 878–883; Frederickson (1999) Nature Biotechnology A, 852–853). FUS1 is a gene whose expression in wild-type cells of the yeast *Saccharomyces cerevisae* is increased, after activation with pheromone α. In U.S. Pat. No. 5,063,153, FUS1 and FUS2 promoters are used in order to express in large amounts a structural gene which codes for a protein of interest.

It was an object of the present invention to identify a different *S. cerevisiae* promoter which can be activated by pheromone α and which can be used to achieve strong expression of the regulated gene.

The invention relates to the promoter of the *S. cerevisiae* YNL279w gene. The invention relates to the promoter having the sequence SEQ ID NO. 4.

The invention also relates to a recombinant DNA fragment containing the *Saccharomyces cerevisiae* YNL 279w gene promoter which, when functionally linked to a structural gene, regulates transcription thereof and to a recombinant DNA fragment containing a promoter having the DNA sequence nucleotides 1 to 505 of SEQ ID NO:4. The invention relates to a recombinant DNA fragment which contains the YNL 279w promoter and a structural gene and in which the promoter is functionally linked to the structural gene. The structural gene codes, for example, for a receptor gene or for a protein which is intended to be produced in large quantities in *S. cerevisiae.*

The invention relates to a DNA vector and a recombinant *S. cerevisiae* cell, which contain such a recombinant DNA fragment. Such a recombinant *S. cerevisiae* cell preferably expresses no or only small quantities of functionally active endogenous receptors Ste2p and Ste3p.

The invention also relates to methods for functional characterization of GPCRs and for screening of GPCR inhibitors and/or activators and to methods for preparing proteins in *S. cerevisiae.*

For example, methods for identifying activators and/or inhibitors of G protein-coupled receptors, wherein a) a recombinant *S. cerevisiae* cell is produced, which contains a reporter gene under the control of the promoter of the YNL 279 w gene and which expresses a heterologous G protein-coupled receptor;

b) the cell is incubated with a substance to be studied, and c) the change in reporter gene transcription is determined.

Methods for identifying constitutively active mutants of G protein-coupled receptors, wherein a) a recombinant *S. cerevisiae* cell is produced, which contains one or more reporter genes under the control of the promoter of the YNL279w gene b) and which expresses a mutated heterologous G protein-coupled receptor, the modification resulting in a constitutively active G protein-coupled receptor, c) the cell is incubated with an activating or inhibiting substance, and d) the change in reporter gene transcription is determined.

In the recombinant *S. cerevisiae* cell, the appropriate endogenous GPCRs, Ste2p and/or Ste3p, are preferably not expressed, for example because these genes have been deleted. This deletion may be carried out as described, for example, in Broach Thorner (1996) Nature, 384, 14–16.

Another embodiment relates to methods for preparing heterologous proteins in *S. cerevisiae,* wherein the structural gene of the heterologous protein to be expressed is functionally linked to the promoter of the YNL279w gene and is expressed under the control thereof.

BRIEF DESCRIPTION OF THE DRAWINGS

Figure 1B-1:
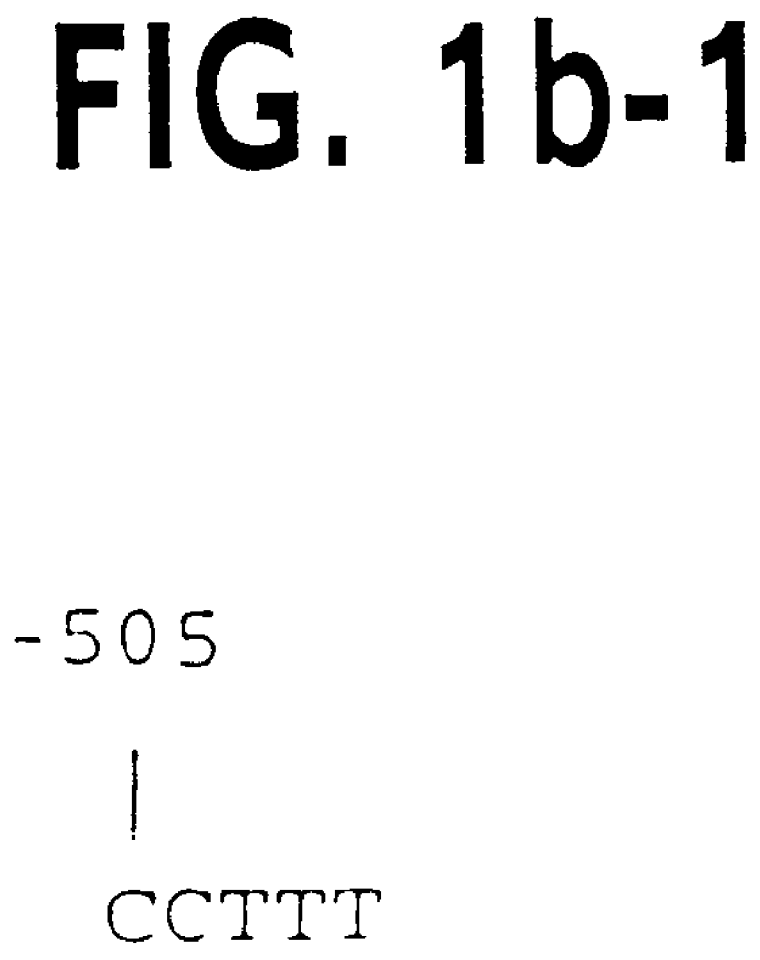

FIG. 1*a:* Sequence of YNL 279w (GenBank acc. No.:Z71555, SEQ ID NO. 3). The ATG startcodon is underlined. Sequence regions in bold type represent pheromone-responsive elements (PRE).

FIG. 1*b:* Promoter region (5'-UTR) of YNL 279w (nucleotides ito 505 of SEQ ID NO:4).

FIG. 1*c:* Pheromone-responsive elements (PRE) in the promoter region of YNL 279w.

FIGS. 4(A)–(B): Induction of aequorin expression (as relative light units) after stimulating the yeast cells with pheromone α at the concentrations stated (B). The values indicated in the diagram represent the averages of three independently carried out experiments, and the corresponding individual values are depicted in (A). In the case of pYNL279-AEQ, the aequorin reporter gene is under the control of the YNL 279w promoter. In the case of 4PRE-AEQ, aequorin is under the control of a region (−271 to −1 before start) of the FUS1 gene. Each stimulation experiment was carried out three times.

DETAILED DESCRIPTION OF THE INVENTION

Pheromone-inducible and -repressible ORFs (open reading frames) were identified by treating cultures of bakers' yeast *Saccharomyces cerevisiae* with or without pheromone α, in order to determine which known genes and, in particular, which as yet uncharacterized genes are induced or repressed by pheromone α. DNA microchips were used, which can display in parallel the expression patterns of the more than 6000 identified yeast genes. Comparison of the gene expression patterns of two cells or cultures of cells which have been treated in different ways, for example with or without pheromone, makes it possible, with the aid of the DNA microarrays after appropriate preparation of the corresponding mRNAs, to determine which genes have been specifically activated or repressed.

Figure 2:
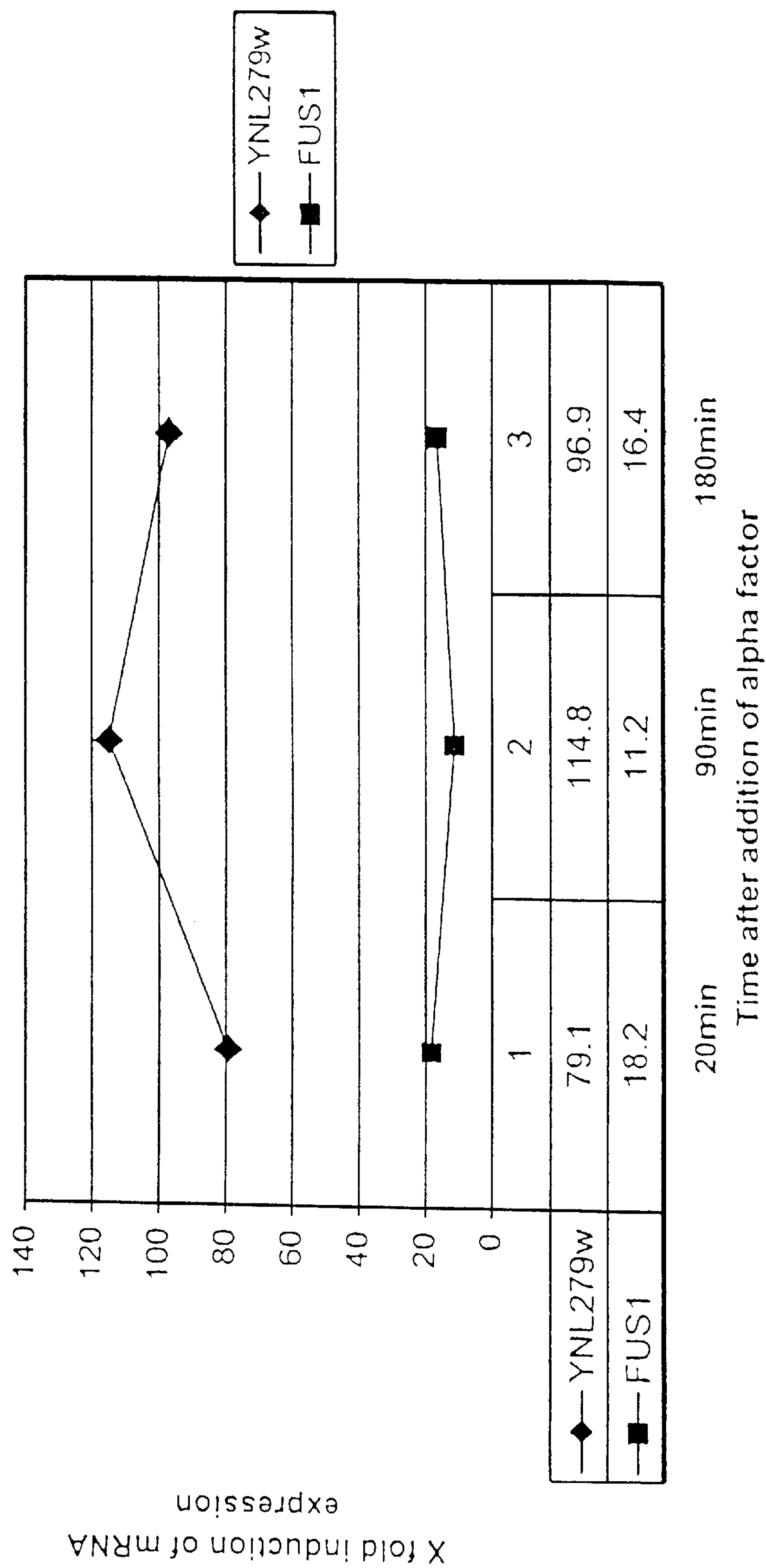
FIG. 2: Expression profile of *Saccharomyces cerevisiae ORE YNL* 279w after induction with pheromone α. The observed changes in gene expression are based on results of the studies using DNA microchips. Changes in gene expression of the FUS1 gene are shown for comparison.
Figure 3:
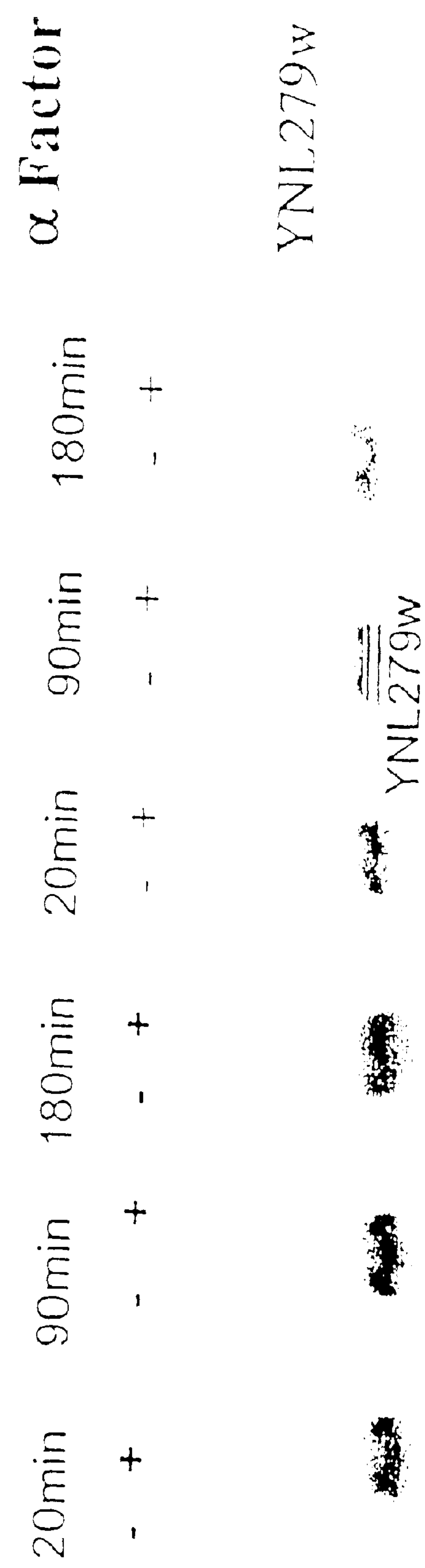
FIG. 3: Northern blot analysis of the expression profile of the YNL 279w gene after stimulating the yeast cultures with pheromone α in yeast mutant sst1.

After addition of pheromone α, ORF YNL279w showed a strong time-dependent increase in its expression (FIGS. 2 and 3). Since transcription and expression of genes are normally regulated via regulatory sequences 5' from the translational starting point, the "promoters", the promoters having such regulatory sequences are of particular interest.

In order to identify activators or inhibitors of pharmacologically and medically interesting GPCRs, it is possible to clone said inducible or repressible promoters in the same way in front of genes or structural genes, which represent a suitable reporter system, in order to identify substances which, after addition, show activating or inhibiting action on the reporter system. Examples of suitable reporter systems are the genes of LacZ, luciferase, aequorin, green fluorescent protein (GFP), DsRed, HIS3, URA3, TRP1 and LEU2, but also resistance genes against particular antibiotics, for example kanamycin.

These "reporter genes" may be, for example, genes such as lacZ, for which an action of particular substances on the MAPK cascade can be detected via color change of the cell colonies. The reporter genes may also be, for example, genes which make it possible for the cell to grow under particular selection conditions such as, for example, auxotrophic genes.

Examples of DNA fragments (DNA constructs) containing the promoter of the YNL279w gene and reporter genes cloned behind said promoter are listed in table 1. Said DNA constructs may be used, for example, for identifying GPCR activators (agonists) and inhibitors (antagonists) in functional assays.

TABLE 1

| DNA construct | Detection system (read out) |
|---|---|
| Promoter(YNL279w)-lacZ | Colorimetric/chemiluminescence read out |
| Promoter(YNL279w)-luciferase | Chemiluminescence read out |
| Promoter(YNL279w)-aeqourin | Chemiluminescence read out |
| Promoter(YNL279w)-GFP | Fluorescent colonies (cells) |
| Promoter(YNL279w)-EGFP | Fluorescent colonies (cells) |
| Promoter(YNL279w)-KAN | Growth in selection medium |
| Promoter(YNL279w)-HIS3 | Growth in histidine-depleted medium |
| Promoter(YNL279w)-URA3 | Growth in uracil-depleted medium |
| Promoter(YNL279w)-TRP1 | Growth in tryptophan-depleted medium |
| Promoter(YNL279w)-LEU2 | Growth in leucine-depleted medium |
| Promoter(YNL279w)-ADE2 | Growth in adenine-depleted medium |
| Promoter(YNL279w)-CAN1 | Growth in canavanine-containing medium (when adding an inhibitor) |

The DNA which codes for such a receptor gene is fused 3' to the pheromone-inducible promoter of ORF YNL279w of the yeast *Saccharomyces cerevisae* and cloned, for example, into a high-copy vector or a low-copy vector. These vectors may then be used for transforming yeast cells. Likewise, it is possible for the DNA fused to the promoter to be stably integrated into the yeast genome.

Yeast strains which are genetically manipulated with reporter genes belonging to the group of auxotrophic genes (e.g. HIS3, URA3, TRP1, LEU2, ADE2 and LYS1) must be mutated, i.e. functionally inactivated, for the corresponding gene.

Stimulation of yeast cells by pheromone leads to activation of the yeast promoter YNL 279 w and to increased expression of the reporter gene regulated by the promoter. When searching for GPCR agonists, the promoter of the gene YNL279w is preferably cloned in front of reporter genes such as, for example, HIS, ADE, TRP or LEU, since this combination allows a read out via cell growth in an appropriately depleted medium. Activation of a selected GPCR by a substance to be studied results in activation of the promoter YNL279w which is at the bottom of the MAPK cascade and thus in expression of the reporter gene regulated by the YNL279w promoter. In the case of HIS, ADE, TRP or LEU, this leads to growth in the corresponding selection medium. An agonist can be identified by the corresponding *S. cerevisiae* cells growing in the selection medium.

When using the genes for LacZ, GFP or EGFP, a read out may be carried out via colorimetric or luminometric measurements. Only those cells whose heterologous GPCR has been activated by an agonist show chemiluminescence.

When the reporter gene used is CAN1, the cells grow in canavanine-containing medium. The CAN1 gene is expressed in the presence of activators (agonists) of a heterologously expressed GPCR so that the cells cease growing in the canavanine-containing medium. If an antagonist (inhibitor) is added, the cultures will grow in said selection medium.

The screening methods may be carried out on microtiter plates seeded with yeast cells which have been transformed beforehand with the promoter-reporter gene construct (e.g. a DNA construct from table 1). In addition, said cells are transformed with a heterologous GPCR for which an agonist or antagonist is to be found. It is possible, for example, to use in said methods human GPCRs, for example adenosine receptors, somatostatin receptors, dopamine receptors, bradykinin receptors, lysolipid receptors, β-adrenergic receptors and muscarinic acetylcholine receptors.

As a pheromone α-induced gene, the YNL279w promoter may also be used for identifying activators and inhibitors of the pheromone-dependent MAPK cascade. Since the YNL279w promoter is, after pheromone α treatment, more sensitive to stimulation than, for example, the FUS1 promoter, using the YNL279w promoter, as proposed herein, is advantageous compared with other screening methods using, for example, the FUS1 promoter. FIG. 4 shows that stimulation of the YNL279w promoter/aequorin construct (p415YNL279-AEQ) reacts substantially better than is the case for a promoter element corresponding to a region from the promoter of the FUS1 gene (denoted 4PRE-AEQ here).

FIG. 2: Expression profile of *Saccharomyces cerevisiae* ORF YNL279w after induction with pheromone α. The observed changes in gene expression are based on results of the studies using DNA microchips. Changes in gene expression of the FUS1 gene are shown for comparison.

FIG. 3: Northern blot analysis of the expression profile of the YNL279w gene after stimulating the yeast cultures with pheromone α in yeast mutant sst1.

Figure 4B:
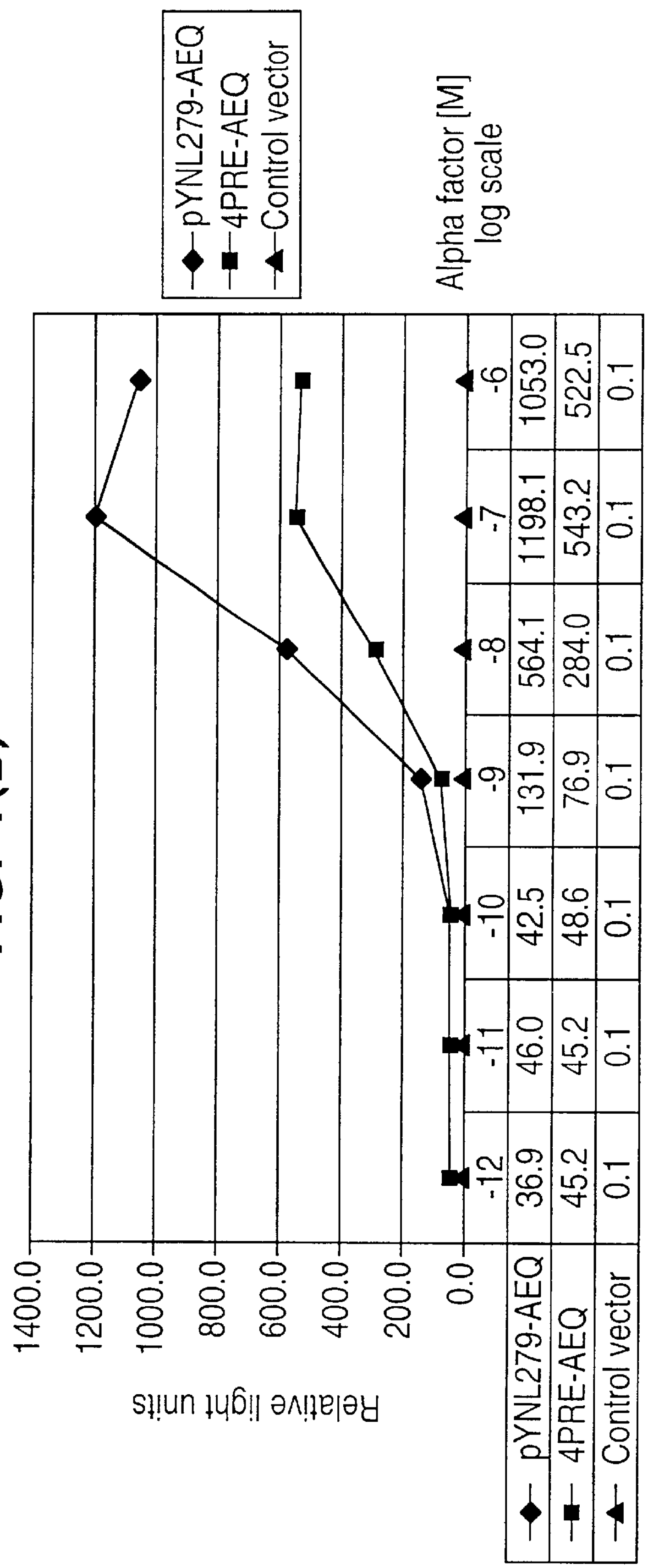

FIGS. 4(A)–(B): Induction of aequorin expression (as relative light units) after stimulating the yeast cells with pheromone α at the concentrations stated (B). The values indicated in the diagram represent the averages of three independently carried out experiments, and the corresponding individual values are depicted in (A). In the case of pYNL279-AEQ, the aequorin reporter gene is under the control of the YNL279w promoter. In the case of 4PRE-AEQ, aequorin is under the control of a region (−271 to −1 before start) of the FUS1 gene. Each stimulation experiment was carried out three times.

Figure 5:
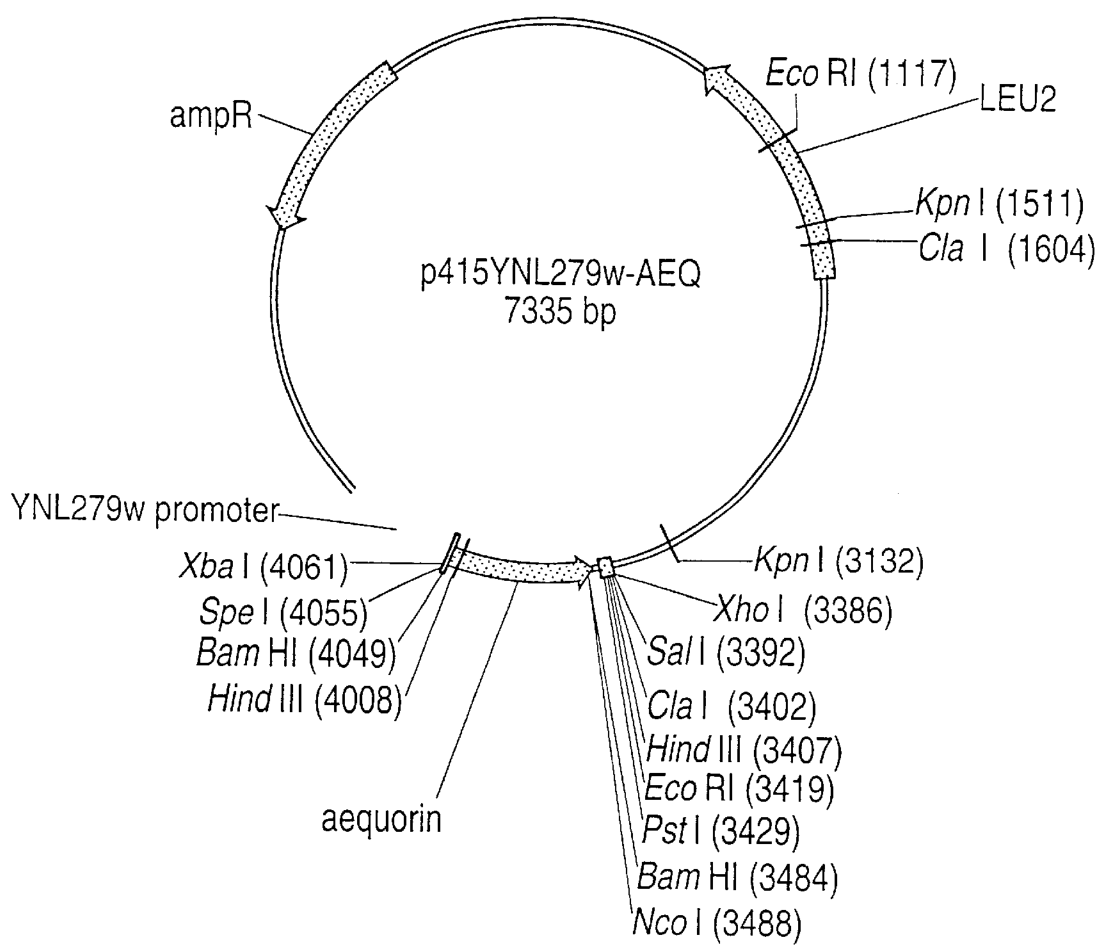
FIG. 5: Diagrammatic representation of the promoter-reporter gene vector construct comprising the YNL 279w promoter region and the aeqourin reporter gene in vector p415 (a derivative of vector pRS415: ATCC 87520).

FIG. 5: Diagrammatic representation of the promoter-reporter gene vector construct comprising the YNL279w promoter region and the aeqourin reporter gene in vector p415 (a derivative of vector pRS415: ATCC 87520).

EXAMPLES

Example 1

Identification of ORF YN279w

Cell cultures of the *Saccharomyces cerevisiae* yeast strain having the genotype (MAT a sst1::LEU2; ade2; can1–100; his3–11, 15; leu2–3, 112; trp1–1; ura3–1 )were stimulated with 1 μM pheromone α (dissolved in 90% methanol); control cells were treated only with 90% methanol. 20 min, 90 min and 180 min after stimulation, an amount of cells corresponding to about 10 $OD_{600\ nm}$ was removed. Total RNA from these cells was isolated according to standard methods (e.g. Sambrook et al. Molecular Cloning, Chemistry Press, (Cold Spring Harbor Laboratory 1989), and in each case 30 μg of total RNA were use for first strand synthesis. The protocol for first and second strand synthesis and also for the purification steps of the double-stranded cDNA generated, the in-vitro transcription and preparation of cRNA for hybridization corresponds to the protocol from Affymetrix Inc. (Santa Clara, Calif., USA).

The YNL279w ORF was identified, via comparison of the expression profiles of pheromone α-induced and noninduced yeast cells, as one of the ORFs induced most strongly.

The activity and usability of the promoter in a screening system with a suitable reporter was determined by amplifying the YNL279w promoter region from genomic *Saccharomyces cerevisiae* DNA.

Beispiel 2

Isolation of the YNL279w Promoter ("Promoter")

The promoter region of the YNL279w gene was amplified using primers YNL279F1 (SEQ ID NO. 1; 5'-CCGAGTCCTACTCCTATGCTGTTTACAAGG-3') and YNL279R (SEQ ID NO. 2; 5'-TGCTCTAGAATCATCAACGTTCACAAATTCG-3').

The identity of the resulting amplificate was determined by standard sequencing methods.

The length of the promoter region amplified via YNL279F1/YNL279R is 473 bp without restriction cleavage sites; this fragment of the promoter region is denoted "promoter" below.

Example 3

Determination of Functionality

The functionality of the proposed screening method was determined by cloning the amplified promoter region of the YNL279w gene into vector p415 (see FIG. 5; derivative of vector pRS415, ATCC 87520) in front of the aequorin-encoding gene. This construct was transformed into the *Saccharomyces cerevisiae* strain (Mat a far1::hisG sst2::ura3$^{FOA}$ fus1::HIS3) using the Li acetate method (Ito et al., 1983). After stimulating the MAPK cascade in the *Saccharomyces cerevisiae* strain (Mat a far1::hisG sst2::ura3$^{FOA}$ fus1::HIS3) with pheromone α, aequorin was detected as follows:

1. 25 μl of cell suspension (1.5×10$^6$ cells per 25 pi in selection medium, SC/glucose leucine) were added to a well of a 96-well plate;
2. 25 μl of a 2×concentrated stimulation mix containing mating factor α in serial dilution (10$^{-6}$ M to 10$^{-8}$ M) and 1 μM coelenterazine (final concentration 0.5 μM) were added to the cells;
3. the 96-well plate is carefully agitated;
4. the 96-well plate is incubated in a humid atmosphere at 30° C. in the dark for 1.5 hours;
5. for detection, 150 μl of calcium/lysis buffer are added; aequorin emits photons immediately after adding this mix; the resulting signal is integrated for 15 s; the signal is detected by means of a luminometer (Luminoskan, LABSYSTEM)

Mating factor α stock solution: 100 μM in 90% methanol

Coelenterazine stock solution: 1 mM in 100% methanol (MOLECULAR PROBES; ref C-2944)

$CaCl_2$ stock solution: 1 M in 1 M Tris-HCl solution (diluted 100 fold in lysis buffer prior to use)

Lysis buffer: yeast protein extraction reagent; PIERCE, ref 78990

References

Cismowski M J, Takesono A, Ma C, Lizano J S, Xie X, Fuernkranz H, Lanier S M, Duzic E. (1999) Genetic screens in yeast to identify mammalian nonreceptor modulators of G-protein signaling. Nat Biotechnol 17:878–83

Erdman S, Lin L, Malczynski M, Snyder M. (1998) Pheromone-regulated genes required for yeast mating differentiation. J Cell Biol 140:461–83

Fink, G R, Trueheart, J, Elion, E A. (1991) Pheromone-inducible yeast promoter. U.S. Pat. No. 5,063,154

Frederickson R M. (1999) Budding actors in mammalian G-protein signaling. Nat Biotechnol 17:852–3

Geras-Raaka E, Varma A, Ho H, Clark-Lewis I, Gershengorn M C. (1998) Human interferon-gamma-inducible protein 10 (IP-10) inhibits constitutive signaling of Kaposi's sarcoma-associated herpesvirus G protein-coupled receptor. J Exp Med 188:405–8

Gustin M C, Albertyn J, Alexander M, Davenport K. (1998) MAP kinase pathways in the yeast *Saccharomyces cerevisiae.* Microbiol Mol Biol Rev 62:1264–300

Stadel J M, Wilson, S, Bergsma, D J. (1997) Orpahn G protein-coupled receptors: a neglected opportunity for pioneer drug discovery. TiPS 18:430–437

Wilson S, Bergsma D J, Chambers J K, Muir Al, Fantom K G, Ellis C, Murdock P R, Herrity N C, Stadel J M (1998) Orphan G-protein-coupled receptors: the next generation of drug targets? Br J Pharmacol 125:1387–92

Wodicka L, Dong H, Mittmann M, Ho M H, Lockhart D J. (1997) Genome-wide expression monitoring in *Saccharomyces cerevisiae.* Nat Biotechnol 15:1359–67

Ito H, Fukuda Y, Murata K, Kimura A (1983) Transformation of intact yeast cells treated with alkali cations. J Bacteriol Jan;153:163–8

Ross-Macdonald P, Coelho P S, Roemer T, Agarwal S, Kumar A, Jansen R, Cheung K H, Sheehan A, Symoniatis D, Umansky L, Heidtman M, Nelson F K, Iwasaki H, Hager K, Gerstein M, Miller P, Roeder G S, Snyder M (1999) Large-scale analysis of the yeast genome by transposon tagging and gene disruption. Nature 402:413–8

We claim:

1. A recombinant DNA fragment comprising the isolated *Saccharomyces cerevisiae* YNL 279w gene promoter region having the nucleotide sequence set forth at positions 1 to 505 of SEQ ID NO:4 which, when functionally linked to a structural gene, regulates transcription thereof.

2. The recombinant DNA fragment as claimed in claim 1, comprising the isolated promoter region and a structural gene, wherein the promoter region is functionally linked to the structural gene and regulates expression thereof.

3. The recombinant DNA fragment as claimed in claim 2, wherein the structural gene codes for a reporter gene.

4. The recombinant DNA fragment as claimed in claim 3, wherein the reporter gene is selected from lacZ, luciferase, aequorin, GFP, dsRed, HIS 3, URA 3, TRP 1 and LEU 2.

5. A DNA vector comprising a recombinant DNA fragment as claimed in claim 1.

6. A DNA vector comprising a recombinant DNA fragment as claimed in claim 2.

7. A DNA vector comprising a recombinant DNA fragment as claimed in claim 3.

8. A DNA vector comprising a recombinant DNA fragment as claimed in claim 4.

9. A recombinant *S. cerevisiae* cell comprising a recombinant DNA fragment as claimed in claim 1.

10. A recombinant *S. cerevisiae* cell comprising a recombinant DNA fragment as claimed in claim 2.

11. A recombinant *S. cerevisiae* cell comprising a recombinant DNA fragment as claimed in claim 3.

12. A recombinant *S. cerevisiae* cell comprising a recombinant DNA fragment as claimed in claim 4.

* * * * *